(12) United States Patent
Xian et al.

(10) Patent No.: US 8,293,519 B2
(45) Date of Patent: *Oct. 23, 2012

(54) MICROARRAY DEVICES HAVING CONTROLLABLE REACTION VOLUME

(75) Inventors: Feijun Xian, Beijing (CN); Wanli Xing, Beijing (CN); Jing Cheng, Beijing (CN); Dong Liang, Beijing (CN); Liang Zhang, Beijing (CN); Dong Wang, Beijing (CN)

(73) Assignees: Capitalbio Corporation, Beijing (CN); Tsinghua University, Beijing (CN)

( * ) Notice: Subject to any disclaimer, the term of this patent is extended or adjusted under 35 U.S.C. 154(b) by 1092 days.

This patent is subject to a terminal disclaimer.

(21) Appl. No.: 10/566,329

(22) PCT Filed: Aug. 13, 2003

(86) PCT No.: PCT/CN03/00667
§ 371 (c)(1),
(2), (4) Date: Sep. 15, 2006

(87) PCT Pub. No.: WO2005/012561
PCT Pub. Date: Feb. 10, 2005

(65) Prior Publication Data
US 2007/0054273 A1  Mar. 8, 2007

(30) Foreign Application Priority Data
Aug. 1, 2003  (CN) .................. 03 1 50086

(51) Int. Cl.
*C12M 1/36* (2006.01)
*G01N 15/06* (2006.01)
*B01L 3/00* (2006.01)

(52) U.S. Cl. ............... 435/283.1; 435/287.2; 435/288.4; 435/288.5; 422/68.1; 422/501; 422/503

(58) Field of Classification Search ........................ None
See application file for complete search history.

(56) References Cited

U.S. PATENT DOCUMENTS

| | | | |
|---|---|---|---|
| 6,159,727 A | 12/2000 | Bochkariov | |
| 6,258,593 B1 | 7/2001 | Schembri et al. | |
| 6,403,368 B1 | 6/2002 | Jan et al. | |
| 6,423,552 B1 | 7/2002 | Lu et al. | |
| 6,485,918 B1 | 11/2002 | Schermer et al. | |

(Continued)

FOREIGN PATENT DOCUMENTS
CA  2215561  3/1998
(Continued)

OTHER PUBLICATIONS

Notice of Reasons for Rejection for Japanese Patent Application No. 2005-507346, mailed on Feb. 25, 2009, 6 pages.

(Continued)

*Primary Examiner* — Betty Forman
(74) *Attorney, Agent, or Firm* — Morrison & Foerster LLP

(57) ABSTRACT

This invention relates generally to the field of microarray chips and uses thereof. In particular, the invention provides a microarray reaction device that can be used in assaying the interaction between various moieties, e.g., nucleic acids, immunoreactions involving proteins, interactions between a protein and a nucleic acid, a ligand-receptor interaction, and small molecule and protein or nucleic acid interactions, etc. Articles of manufacture and kits comprising the microarray reaction device and assaying methods using the microarray reaction device are also provided.

30 Claims, 7 Drawing Sheets

U.S. PATENT DOCUMENTS

| | | | |
|---|---|---|---|
| 7,025,120 B2 * | 4/2006 | Oldenburg | 165/11.1 |
| 7,063,979 B2 * | 6/2006 | MacBeath et al. | 435/305.2 |
| 7,332,328 B2 * | 2/2008 | Webb et al. | 435/287.2 |
| 7,390,463 B2 * | 6/2008 | He et al. | 422/504 |
| 7,767,438 B2 * | 8/2010 | Xing et al. | 435/287.2 |
| 2001/0010917 A1 | 8/2001 | Bertling | |
| 2002/0102186 A1 | 8/2002 | McEntee et al. | |
| 2002/0155481 A1 | 10/2002 | Hirota et al. | |
| 2003/0059349 A1 | 3/2003 | Howe | |
| 2003/0087292 A1 | 5/2003 | Chen et al. | |
| 2003/0157523 A1 | 8/2003 | Frantz et al. | |
| 2003/0235825 A1 * | 12/2003 | Shea et al. | 435/6 |
| 2004/0091939 A1 | 5/2004 | Cheung et al. | |
| 2004/0126766 A1 | 7/2004 | Amorese | |
| 2006/0141610 A1 | 6/2006 | Xing et al. | |

FOREIGN PATENT DOCUMENTS

| | | |
|---|---|---|
| CN | 1193049 | 9/1998 |
| CN | 1261669 | 8/2000 |
| CN | 1267089 | 9/2000 |
| CN | 1290752 | 4/2001 |
| CN | 1335501 | 2/2002 |
| CN | 2478109 | 2/2002 |
| EP | 0 681 024 | 11/1995 |
| GB | 2 349 349 | 11/2000 |
| JP | 2002517219 | 6/2002 |
| JP | 2003021635 | 1/2003 |
| JP | 2003530545 | 10/2003 |
| WO | WO-99/39829 | 8/1999 |
| WO | WO-01/02094 | 1/2001 |
| WO | WO 02/00336 * | 1/2002 |
| WO | WO-02/24952 | 3/2002 |
| WO | WO-02/072423 | 9/2002 |
| WO | WO-02/087763 | 11/2002 |
| WO | WO-03/031976 | 4/2003 |
| WO | WO-2004/074835 | 9/2004 |

OTHER PUBLICATIONS

International Search Report for PCT/CN03/00667, mailed on Jul. 29, 2004, 3 pages.

Langan et al., (eds.) Ligand Assay, Masson Publishing, New York (1981) pp. 211.

* cited by examiner

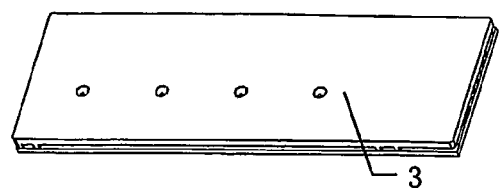
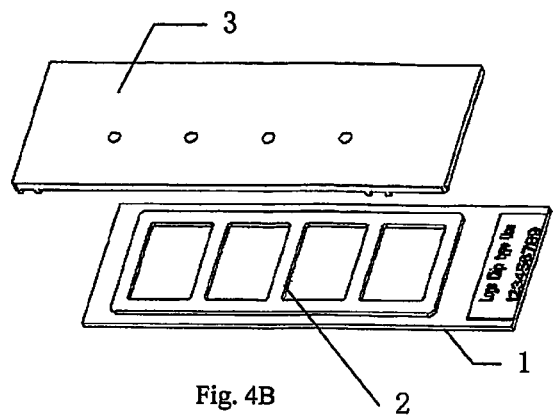
Fig. 4A  Fig. 4B
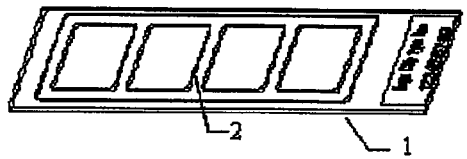
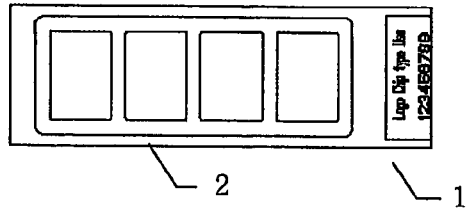
Fig. 5A  Fig. 5B
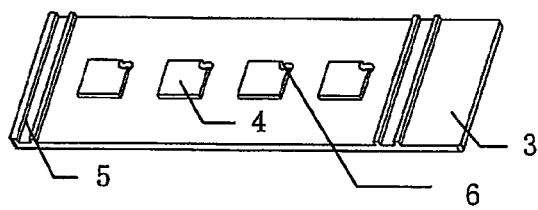
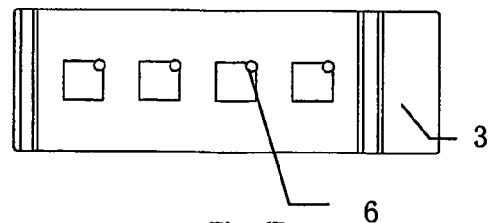
Fig. 6A  Fig. 6B

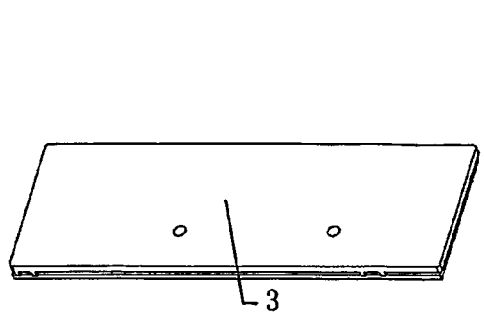
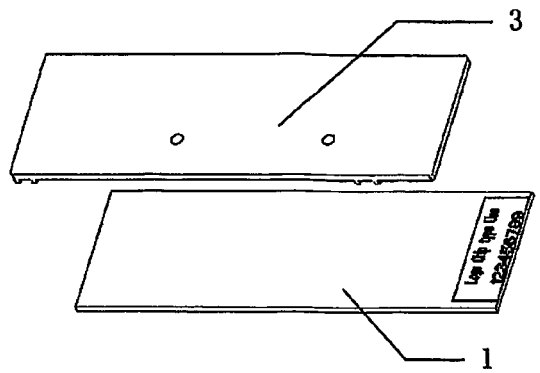
Fig. 10AFig. 10B
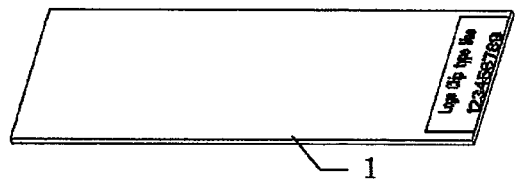
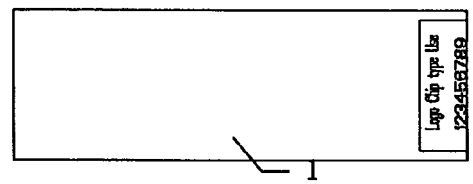
Fig. 11AFig. 11B
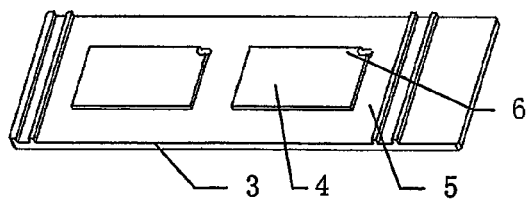
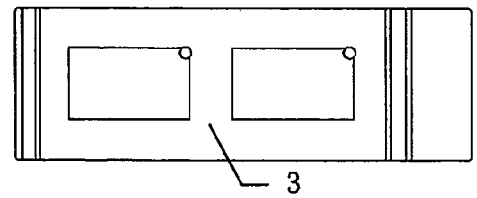
Fig. 12AFig. 12B

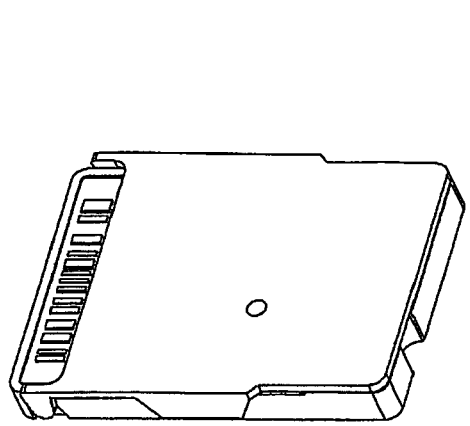
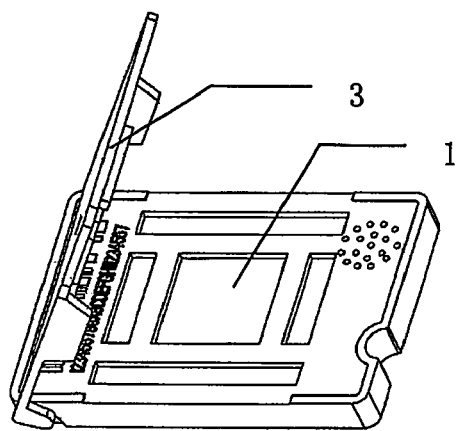
Fig. 13A　　　　　　　　　Fig. 13B
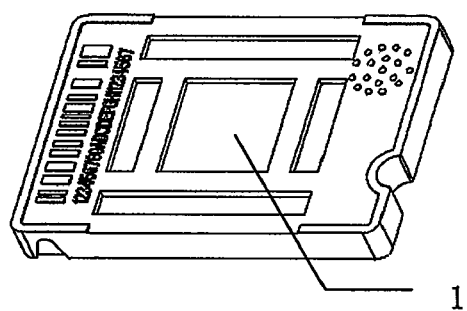
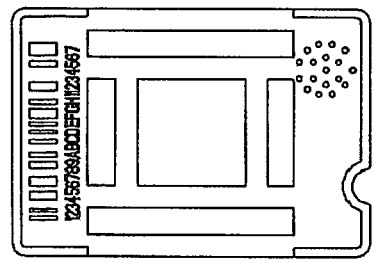
Fig. 14A　　　　　　　　　Fig. 14B
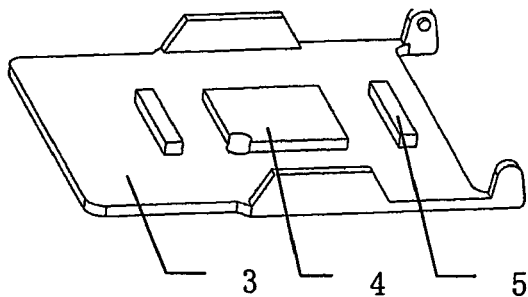
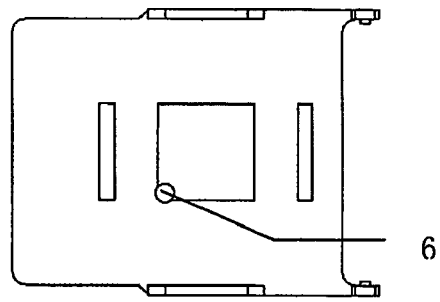
Fig. 15A　　　　　　　　　Fig. 15B

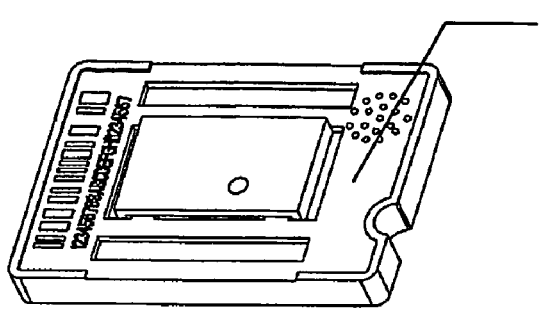
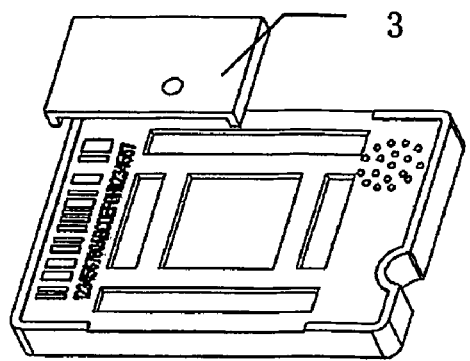
Fig. 16A　　　　　　　　　Fig. 16B
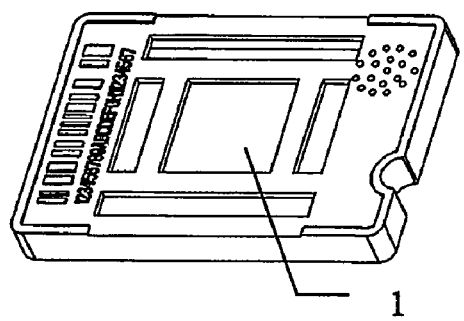
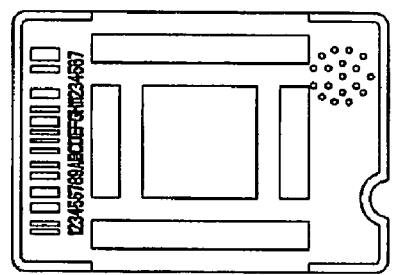
Fig. 17A　　　　　　　　　Fig. 17B
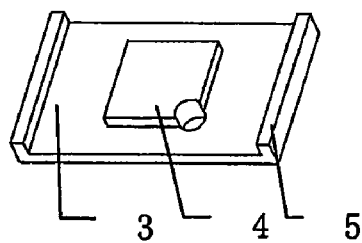
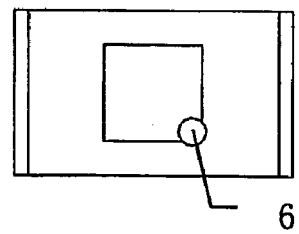
Fig. 18A　　　　　　　　　Fig. 18B

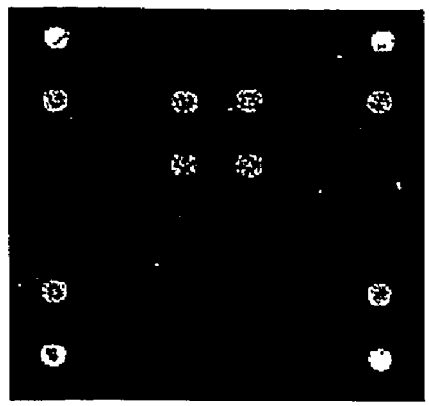 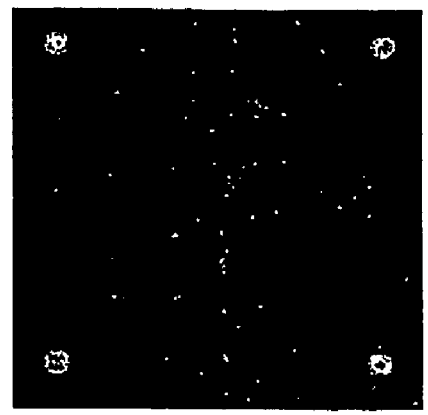
Fig. 19A   Fig. 19B
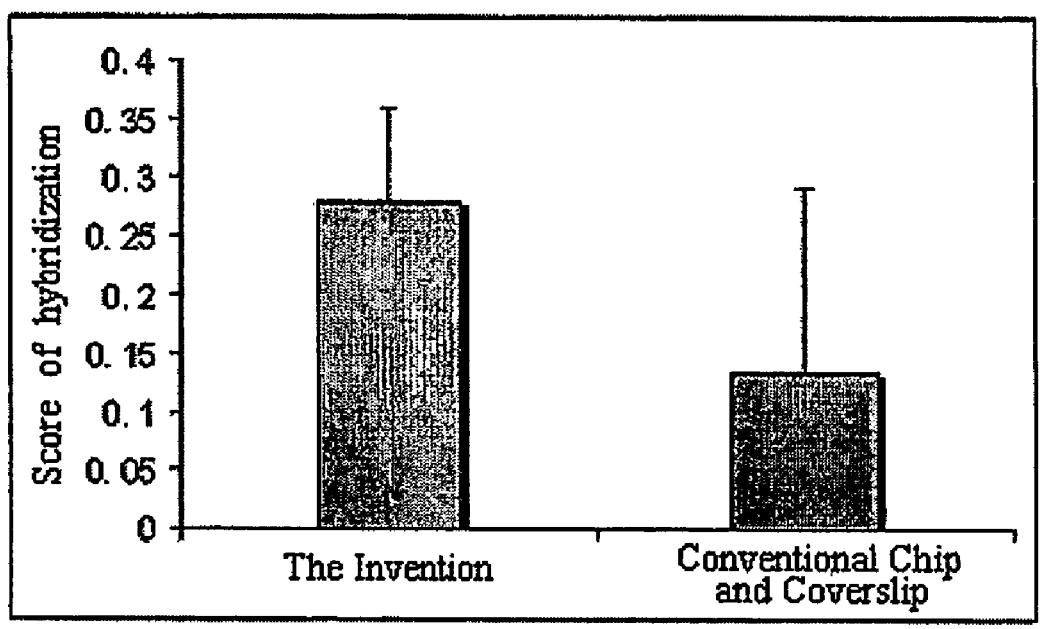
Fig. 19C

MICROARRAY DEVICES HAVING CONTROLLABLE REACTION VOLUME

CROSS-REFERENCE TO RELATED APPLICATIONS

This application is the national phase of PCT application PCT/CN2003/000667 having an international filing date of Aug. 13, 2003, which claims priority from China application number 03150086.2 filed Aug. 1, 2003. The contents of these documents are incorporated herein by reference.

TECHNICAL FIELD

This invention relates generally to the field of microarray chips and uses thereof. In particular, the invention provides a microarray reaction device that can be used in assaying the interaction between various moieties, e.g., nucleic acids, immunoreactions involving proteins, interactions between a protein and a nucleic acid, a ligand-receptor interaction, and small molecule and protein or nucleic acid interactions, etc. Articles of manufacture and kits comprising the microarray reaction device and assaying methods using the microarray reaction device are also provided.

BACKGROUND ART

Taking a gene chip as an example, current microarray chip is comprised of a substrate and a coverslip. The substrate is often a standard slide with the size of 1 inch by 3 inch and the coverslip is often flat plastic or glass plates. There exist several shortcomings for the microarray chip. First, because the depth of hybridization solutions is very short, relatively less molecules can join hybridization reactions, resulting in lower hybridization signals. Second, because a standard-sized slide is used, a relatively large amount of sample is needed to cover the slide, which may waste precious or expensive samples. Third, when multiple samples are analyzed on a single slide, cross-contamination can easily occur and reduce reliability of the assay. Fourth, when multiple samples are analyzed on a single slide, it is often necessary to search for microarray locations for attaching probes thereupon, rendering the operation inconvenient, reducing speed and reliability of assay. Fifth, after the hybridization solution is injected to the slide, the coverslip is then positioned to the slide, requiring users to take enough cares to avoid producing bubbles.

The present invention addresses the above and other related concerns in the art.

DISCLOSURE OF THE INVENTION

In one aspect, the present invention is directed to a microarray reaction device, which device comprises: a) a microarray chip comprising a plurality of microarray areas; and b) a cover comprising a plurality of projections and a supporting structure; wherein a plurality of reaction spaces are formed between said microarray areas of said microarray chip and said projections of said cover, and the volumes of said reaction spaces are substantially identical and controllable by the height of said supporting structure and the areas of said projections.

In another aspect, the present invention is directed to an article of manufacture, which article of manufacture comprises: a) packaging material; b) an above-described microarray reaction device; and c) a label indicating that the article is for assaying an analyte.

In still another aspect, the present invention is directed to a method for assaying an analyte, which method comprises: a) providing an above-described microarray reaction device; b) attaching a plurality of reactants to said plurality of microarray areas and/or said plurality of projections of said microarray reaction device provided in a), wherein at least one of said reactants is capable of binding to an analyte to be analyzed; c) contacting a sample suspected of containing said analyte with said reactant(s) provided in step a) under suitable conditions to allow binding of said analyte, if present in said sample, to said reactant(s); and d) assessing binding between said analyte to said reactant(s) to determine presence and/or amount of said analyte in said sample.

In yet another aspect, the present invention is directed to a kit for assaying an analyte, which kit comprises: a) an above-described microarray reaction device; b) means for attaching a plurality of reactants to said plurality of microarray areas and/or said plurality of projections of said microarray reaction device provided in a), wherein at least one of said reactants is capable of binding to an analyte to be analyzed; and c) means for assessing binding between said analyte to said reactant(s) to determine presence and/or amount of said analyte in said sample.

In yet another aspect, the present invention is directed to a microarray reaction device, which device comprises: a) a microarray chip comprising a microarray area; and b) a cover comprising a projection and a supporting structure; wherein a reaction space is formed between said microarray area of said microarray chip and said projection of said cover, and the volume of said reaction space is controllable by the height of said supporting structure and the area of said projection.

In yet another aspect, the present invention is directed to a method for assaying an analyte, which method comprises: a) providing an above-described microarray reaction device; b) attaching a reactant to said microarray area and/or said projection of said microarray reaction device provided in a), wherein said reactant is capable of binding to an analyte to be analyzed; c) contacting a sample suspected of containing said analyte with said reactant provided in step a) under suitable conditions to allow binding of said analyte, if present in said sample, to said reactant; and d) assessing binding between said analyte to said reactant to determine presence and/or amount of said analyte in said sample.

In yet another aspect, the present invention is directed to a kit for assaying an analyte, which kit comprises: a) an above-described microarray reaction device; b) means for attaching a reactant to said microarray area and/or said projection of said microarray reaction device provided in a), wherein said reactant is capable of binding to an analyte to be analyzed; and c) means for assessing binding between said analyte to said reactant to determine presence and/or amount of said analyte in said sample.

BRIEF DESCRIPTION OF THE DRAWINGS

FIGS. 1-3 illustrate the first embodiment of the present invention, wherein the microarray chip comprises a slide and an enclosure.

FIGS. 4-6 illustrate the second embodiment of the present invention, wherein the cover comprises a plurality of through-holes to deliver fluid into the reaction spaces. FIG. 4A is an assembly view, and FIG. 4B is an exploded view. FIG. 5A is a three-dimensional view of the microarray chip, and FIG. 5B is a top view. FIG. 6A is a three-dimensional view of the cover, and FIG. 6B is a top view.

FIGS. 7-9 illustrate the third embodiment of the present invention, wherein the cover comprises one projection.

FIGS. 10-12 illustrate the fourth embodiment of the present invention, wherein the cover comprises two projections. FIG. 10A is an assembly view, and FIG. 10B is an exploded view. FIG. 11A is a three-dimensional view of the microarray chip, and FIG. 11B is a top view. FIG. 12A is a three-dimensional view of the cover, and FIG. 12B is a top view.

FIGS. 13-15 illustrate the fifth embodiment of the present invention, wherein the microarray chip comprises one microarray area. FIG. 13A is an assembly view, and FIG. 13B is an exploded view. FIG. 14A is a three-dimensional view of the microarray chip, and FIG. 14B is a top view. FIG. 15A is a three-dimensional view of the cover, and FIG. 15B is a top view.

FIGS. 16-18 illustrate the sixth embodiment of the present invention, wherein the microarray chip comprises one microarray area. FIG. 16A is an assembly view, and FIG. 16B is an exploded view. FIG. 17A is a three-dimensional view of the microarray chip, and FIG. 17B is a top view. FIG. 18A is a three-dimensional view of the cover, and FIG. 18B is a top view.

FIG. 19 is a comparison of the second embodiment of the present invention with a conventional slide and coverslip device. FIG. 19A is an image of hybridization results acquired by using the second embodiment of the present invention. FIG. 19B is an image of hybridization results acquired by using the conventional slide and coverslip device. FIG. 19C is a diagram illustrating quantitative difference between the results shown in FIGS. 19A and 19B.

MODES FOR CARRYING OUT THE INVENTION

Figure 1A:
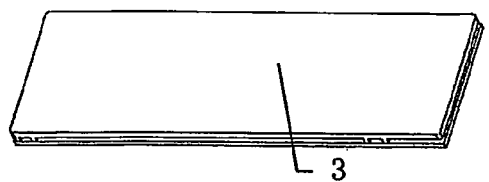
FIG. 1A is an assembly view.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "microarray chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips can vary considerably, e.g., from about 1 mm$^2$ to about 0.25 m$^2$. Preferably, the size of the chips is from about 4 mm$^2$ to about 25 cm$^2$ with a characteristic dimension from about 1 mm to about 5 cm. The chip surfaces may be flat, or not flat. The chips with non-flat surfaces may include channels or wells fabricated on the surfaces.

As used herein, "the volumes of said reaction spaces are substantially identical" means that the differences among the volumes of said reaction spaces are sufficiently small not to statistically affect assay uniformity. Normally, the difference between the largest volume and the smallest volume is less than 50% of the largest volume of the reaction space. Preferably, the difference between the largest volume and the smallest volume is less than 40%, 30%, 20%, 10%, 5%, 2%, 1% or less than 1% of the largest volume of the reaction space.

As used herein, "a group of structurally and/or functionally related proteins" refers to a group of proteins, at their natural status, that are structurally linked, located at the same cellular locations, e.g., cellular organelles, located in the same tissues or organs, expressed and/or be functional in the same biological stages, e.g., a particular cell cycle stage or developmental stage, or expressed and/or be functional in the same biological pathway, e.g., a particular metabolism pathway, signal transduction pathway, etc. The "group of structurally and/or functionally related proteins" need only include at least two proteins belonging to the same group. The "group of structurally and/or functionally related proteins" can preferably include more than two proteins belonging to the same group, e.g., a majority of or even all the proteins belonging to the same group.

As used herein, "expressed in a tissue or organ specific manner" refers to a gene expression pattern in which a gene is expressed, either transiently or constitutively, only in certain tissues or organs, but not in other tissues or organs.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein: "stringency of hybridization" in determining percentage mismatch is as follows:
1) high stringency: 0.1×SSPE, 0.1% SDS, 65° C.;
2) medium stringency: 0.2×SSPE, 0.1% SDS, 50° C. (also referred to as moderate stringency); and
3) low stringency: 1.0×SSPE, 0.1% SDS, 50° C.

It is understood that equivalent stringencies may be achieved using alternative buffers, salts and temperatures.

As used herein, "gene" refers to the unit of inheritance that occupies a specific locus on a chromosome, the existence of which can be confirmed by the occurrence of different allelic forms. Given the occurrence of split genes, gene also encompasses the set of DNA sequences (exons) that are required to produce a single polypeptide.

As used herein, "gene chip" refers to an array of oligonucleotides immobilized on a surface that can be used to screen an RNA sample (after reverse transcription) and thus a method for rapidly determining which genes are being expressed in the cell or tissue from which the RNA came.

As used herein, "specific binding" refers to the binding of one material to another in a manner dependent upon the presence of a particular molecular structure. For example, a receptor will selectively bind ligands that contain the chemical structures complementary to the ligand binding site(s).

As used herein, "specific binding pair" refers to any substance, or class of substances, which has a specific binding affinity for the ligand to the exclusion of other substances. In one embodiment, the specific binding pair includes specific binding assay reagents which interact with the sample ligand or the binding capacity of the sample for the ligand in an immunochemical manner. For example, there will be an antigen-antibody or hapten-antibody relationship between reagents and/or the sample ligand or the binding capacity of the sample for the ligand. Additionally, it is well understood in the art that other binding interactions between the ligand and the binding partner serve as the basis of specific binding assays, including the binding interactions between hormones, vitamins, metabolites, and pharmacological agents, and their respective receptors and binding substances. (See e.g., Langan et al. eds., *Ligand Assay*, pp. 211 et seq., Masson Publishing U.S.A. Inc., New York, 1981).

As used herein, "antibody" refers to specific types of immunoglobulin, i.e., IgA, IgD, IgE, IgG, e.g., $IgG_1$, $IgG_2$, $IgG_3$, and $IgG_4$, and IgM. An antibody can exist in any suitable form and also encompass any suitable fragments or derivatives. Exemplary antibodies include a polyclonal antibody, a monoclonal antibody, a Fab fragment, a Fab' fragment, a $F(ab')_2$ fragment, a Fv fragment, a diabody, a single-chain antibody and a multi-specific antibody formed from antibody fragments.

As used herein, "sample" refers to anything which may contain an analyte that can be assayed using the present methods and/or kits. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). Biological tissues may be processed to obtain cell suspension samples. The sample may also be a mixture of cells prepared in vitro. The sample may also be a cultured cell suspension. In case of the biological samples, the sample may be crude samples or processed samples that are obtained after various processing or preparation on the original samples. For example, various cell separation methods (e.g., magnetically activated cell sorting) may be applied to separate or enrich target cells from a body fluid sample such as blood. Samples used for the present invention include such target-cell enriched cell preparation.

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

As used herein, "moiety" encompasses both test moiety and target moiety. Non-limiting examples of moieties include cells, cellular organelles, viruses, particles, molecules, e.g., proteins, DNAs and RNAs, or an aggregate or complex thereof.

As used herein, "small molecule" refers to a molecule that, without forming homo-aggregates or without attaching to a macromolecule or adjuvant, is incapable of generating an antibody that specifically binds to the small molecule. Preferably, the small molecule has a molecular weight that is about or less than 10,000 daltons. More preferably, the small molecule has a molecular weight that is about or less than 5,000 dalton.

B. Microarray Reaction Devices and Articles of Manufacture

In one aspect, the present invention is directed to a microarray reaction device, which device comprises: a) a microarray chip comprising a plurality of microarray areas; and b) a cover comprising a plurality of projections and a supporting structure; wherein a plurality of reaction spaces are formed between said microarray areas of said microarray chip and said projections of said cover, and the volumes of said reaction spaces are substantially identical and controllable by the height of said supporting structure and the areas of said projections.

Any suitable microarray chip can be used in the present microarray reaction devices. For example, the microarray chip can be a slide.

In a preferred embodiment, the microarray chip can further comprise an enclosure to form a plurality of separated microarray areas on the microarray chip and to form a plurality of separated reaction spaces. The enclosure can have any suitable dimensions and shapes. In one example, the thickness of the enclosure ranges from about 0.05 mm to about 50 mm. In another example, the enclosure has a shape selected from the group consisting of a square, a rectangle, a circle, an ellipse, an oval and an irregular shape.

In another preferred embodiment, the cover can further comprise one or more through-holes to deliver fluid into the plurality of reaction spaces. The number of the through-holes can range from about 1 to about 2,500. The microarray reaction device can have identical or different numbers of the through-holes and the projections. The through-holes can have any suitable dimensions and shapes. In one example, the transverse cross-section of the through-holes has a shape selected from the group consisting of a square, a rectangle, a circle, an ellipse, an oval and an irregular shape. In another example, the through-holes have a diameter ranging from about 0.01 mm to about 100 mm.

The present microarray reaction device can have any suitable number of the projections and/or the microarray areas. In one example, the number of the projections and/or the microarray areas ranges from about 2 to about 2,500. In another example, the microarray reaction device has dentical or different number of the projections and the microarray areas.

The projections and the microarray areas can have any suitable dimensions and shapes. In one example, the projections and the microarray areas have identical or different shape(s) and/or surface area(s). In another example, the height of the projections ranges from 0.01 mm to 50 mm. In still another example, the surface of the projections has a shape selected from the group consisting of a square, a rectangle, a circle, an ellipse, an oval and an irregular shape. In yet another example, the surface of the projections has an area ranging from about 0.01 $mm^2$ to about 600 $mm^2$. In yet another example, the plurality of reaction spaces have a height ranging from about 0.001 mm to about 1 mm. In yet another example, the plurality of reaction spaces have a volume ranging from about 0.01 $mm^3$ to about 600 $mm^3$.

The microarray chip, the enclosure, and/or the cover can comprise any suitable material. In one example, the microarray chip, the enclosure, and/or the cover comprises a material selected from the group consisting of a silicon, a plastic, a glass, a ceramic, a rubber, a metal, a polymer, a paper and a combination thereof. In another example, the cover comprises a plastic. Preferably, the cover is injection molded. Also preferably, the plastic is selected from the group consisting of polycarbonate, methylmethacrylate, polystyrene, acrylonitrile-butadiene-styrene (ABS), polyethylene and polypropylene. In still another example, the cover comprises a glass. Preferably, the cover is fabricated by a method selected from the group consisting of gluing, dicing/cutting, slicing, anodic bonding, ultrasonic welding, and a combination thereof. In yet another example, the enclosure comrises a rubber attached to a double-coated tape. Preferably, the enclosure is fabricated by stamping. Also preferably, the rubber is selected from the group consisting of silicone, caoutchouc, butyl, urethane and neoprene. In yet another example, the enclosure comrises a single coated tape. Preferably, the enclosure is fabricated by stamping.

The present microarray reaction devices can further comprise substances that are useful in assaying for analytes. For example, the present microarray reaction devices can further comprise a reactant capable of binding to an analyte that is immobilized in a microarray area.

In another aspect, the present invention is directed to an article of manufacture, which article of manufacture comprises: a) packaging material; b) an above-described microarray reaction device; and c) a label indicating that the article is for assaying an analyte.

In yet another aspect, the present invention is directed to a microarray reaction device, which device comprises: a) a microarray chip comprising a microarray area; and b) a cover comprising a projection and a supporting structure; wherein a reaction space is formed between said microarray area of said microarray chip and said projection of said cover, and the volume of said reaction space is controllable by the height of said supporting structure and the area of said projection. An article of manufacture, comprising: a) packaging material; b) an above-described microarray reaction device; and c) a label indicating that the article is for assaying an analyte, is also contemplated.

C. Methods and Kits for Assaying an Analyte

In still another aspect, the present invention is directed to a method for assaying an analyte, which method comprises: a) providing a microarray reaction device described in the above Section B; b) attaching a plurality of reactants to said plurality of microarray areas and/or said plurality of projections of said microarray reaction device provided in a), wherein at least one of said reactants is capable of binding to an analyte to be analyzed; c) contacting a sample suspected of containing said analyte with said reactant(s) provided in step a) under suitable conditions to allow binding of said analyte, if present in said sample, to said reactant(s); and d) assessing binding between said analyte to said reactant(s) to determine presence and/or amount of said analyte in said sample.

In yet another aspect, the present invention is directed to a kit for assaying an analyte, which kit comprises: a) a microarray reaction device described in the above Section B; b) means for attaching a plurality of reactants to said plurality of microarray areas and/or said plurality of projections of said microarray reaction device provided in a), wherein at least one of said reactants is capable of binding to an analyte to be analyzed; and c) means for assessing binding between said analyte to said reactant(s) to determine presence and/or amount of said analyte in said sample.

The kit can further comprise a plurality of reactants, wherein at least one of the reactants is capable of binding to an analyte to be analyzed. The kit can also further comprise an instruction for using the kit to assay the analyte.

In yet another aspect, the present invention is directed to a method for assaying an analyte, which method comprises: a) providing a microarray reaction device, which device comprises a microarray chip comprising a microarray area, a cover comprising a projection and a supporting structure, and wherein a reaction space is formed between said microarray area of said microarray chip and said projection of said cover, and the volume of said reaction space is controllable by the height of said supporting structure and the area of said projection; b) attaching a reactant to said microarray area and/or said projection of said microarray reaction device provided in a), wherein said reactant is capable of binding to an analyte to be analyzed; c) contacting a sample suspected of containing said analyte with said reactant provided in step a) under suitable conditions to allow binding of said analyte, if present in said sample, to said reactant; and d) assessing binding between said analyte to said reactant to determine presence and/or amount of said analyte in said sample.

In yet another aspect, the present invention is directed to a kit for assaying an analyte, which kit comprises: a) a microarray reaction device, which device comprises a microarray chip comprising a microarray area, a cover comprising a projection and a supporting structure, and wherein a reaction space is formed between said microarray area of said microarray chip and said projection of said cover, and the volume of said reaction space is controllable by the height of said supporting structure and the area of said projection; b) means for attaching a reactant to said microarray area and/or said projection of said microarray reaction device provided in a), wherein said reactant is capable of binding to an analyte to be analyzed; and c) means for assessing binding between said analyte to said reactant to determine presence and/or amount of said analyte in said sample.

The present methods and kits can be used to assay any analyte, e.g., a cell, a cellular organelle, a virus, a molecule and an aggregate or complex thereof. Exemplary cells include animal cells, plant cells, fungus cells, bacterium cells, recombinant cells and cultured cells. Animal, plant, fungus, bacterium cells can be derived from any genus or subgenus of the Animalia, Plantae, fungus or bacterium kingdom. Cells derived from any genus or subgenus of ciliates, cellular slime molds, flagellates and microsporidia can also be assayed by the present methods. Cells derived from birds such as chickens, vertebrates such as fish and mammals such as mice, rats, rabbits, cats, dogs, pigs, cows, ox, sheep, goats, horses, monkeys and other non-human primates, and humans can be assayed by the present methods.

For animal cells, cells derived from a particular tissue or organ can be assayed by the present methods and kits. For example, connective, epithelium, muscle or nerve tissue cells can be assayed. Similarly, cells derived from an accessory organ of the eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl can be used. Preferably, cells derived from an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc can be assayed. Further, cells derived from any plants, fungi such as yeasts, bacteria such as eubacteria or archaebacteria can be assayed. Recombinant cells derived from any eucaryotic or prokaryotic sources such as animal, plant, fungus or bacterium cells can also be assayed. Body fluid such as blood, urine, saliva, bone marrow, sperm or other ascitic fluids, and subfractions thereof, e.g., serum or plasma, can also be assayed.

Exemplary cellular organelles include nuclei, mitochondria, chloroplasts, ribosomes, ERs, Golgi apparatuses, lysosomes, proteasomes, secretory vesicles, vacuoles and microsomes. Exemplary molecules include inorganic molecules, organic molecules and a complex thereof. Exemplary organic molecules include amino acids, peptides, proteins, nucleosides, nucleotides, oligonucleotides, nucleic acids, vitamins, monosaccharides, oligosaccharides, carbohydrates, lipids and a complex thereof.

Any amino acids can be assayed by the present methods and kits. For example, a D- and a L-amino-acid can be assayed. In addition, any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V) can be assayed by the present methods.

Any proteins or peptides can be assayed by the present methods and kits. For example, enzymes, transport proteins such as ion channels and pumps, nutrient or storage proteins, contractile or motile proteins such as actins and myosins, structural proteins, defense protein or regulatory proteins such as antibodies, hormones and growth factors can be assayed. Proteineous or peptidic antigens can also be assayed.

Any nucleic acids, including single-, double and triple-stranded nucleic acids, can be assayed by the present methods and kits. Examples of such nucleic acids include DNA, such as A-, B- or Z-form DNA, and RNA such as mRNA, tRNA and rRNA.

Any nucleosides can be assayed by the present methods and kits. Examples of such nucleosides include adenosine, guanosine, cytidine, thymidine and uridine. Any nucleotides can be assayed by the present methods. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Any vitamins can be assayed by the present methods and kits. For example, water-soluble vitamins such as thiamine, riboflavin, nicotinic acid, pantothenic acid, pyridoxine, biotin, folate, vitamin $B_{12}$ and ascorbic acid can be assayed. Similarly, fat-soluble vitamins such as vitamin A, vitamin D, vitamin E, and vitamin K can be assayed.

Any monosaccharides, whether D- or L-monosaccharides and whether aldoses or ketoses, can be assayed by the present methods and kits. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any lipids can be assayed by the present methods and kits. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

The present method and kits can be used to assay any sample. For example, the present method can be used to assay a mammalian sample. Exemplary mammals include bovines, goats, sheep, equines, rabbits, guinea pigs, murine, humans, felines, monkeys, dogs and porcines. The present method can also be used to assay a clinical sample. Exemplary clinical samples include serum, plasma, whole blood, sputum, cerebral spinal fluid, amniotic fluid, urine, gastrointestinal contents, hair, saliva, sweat, gum scrapings and tissue from biopsies. Preferably, the present method can be used to assay a human clinical sample.

Any suitable reactant(s) can be used in the present methods and kits. Preferably, the reactant(s) used in the present methods binds specifically with the analyte. Exemplary reactants include cells, cellular organelles, viruses, molecules and an aggregate or complex thereof. Preferably, the reactant is an antibody. Also preferably, the reactant is a nucleic acid.

The present methods and kits can be used in any suitable assay format. For example, the present methods can be used in a direct assay format, a sandwich assay format or a competition assay format.

In one embodiment, a different plurality of reactants are used to assay a single analyte. In another embodiment, a different plurality of reactants are used to assay a different plurality of analytes. In still another embodiment, a plurality of reactants are attached to the first plurality of projections of the microarray. In yet another embodiment, all reactants are capable of binding to an analyte to be analyzed.

The present methods and kits can be used to detect any interaction(s) among moieties selected from the group consisting of a cell, a cellular organelle, a virus, a molecule and an aggregate or complex thereof. For example, the present methods and kits can be used to detect interactions between or among macromolecules, such as DNA-DNA, DNA-RNA, RNA-RNA, DNA-protein, RNA-protein and protein-protein, etc., interactions. The present methods and kits can also be used to detect macromolecule-small molecule or small molecule-small molecule interactions. The present methods and kits can also be used to detect more complex interactions including interactions among more than two moieties. When DNA-DNA, DNA-RNA, RNA-RNA interactions are to be detected, the contacting, i.e., hybridizing, step, can be conducted under suitable condition, e.g., under low, middle or high stringency.

The interaction between said test moiety and said plurality of target moieties can be detected by any suitable methods. For example, the test moiety and/or target moieties can be labeled to facilitate detection. Any suitable label can be used. Exemplary labels include a radioactive, a fluorescent, a chemical, an enzymatic, a luminescent and a FRET (fluorescence resonance energy transfer) label. The luminescent label can be a chemiluminescent label or a bioluminescent label.

The labels can be attached or conjugated, directly or indirectly, to the test moiety alone, the target moiety alone, or on both. The read-out can be a positive or a negative signal. Any suitable assay formats, including sandwich or competitive formats, can be used.

In a preferred embodiment, the present methods and kits are used to detect interaction between or among a test moiety and a plurality of genes, gene fragments or their encoded products. More preferably, the plurality of target genes, gene fragments or their encoded products are involved in a biological pathway, belong to a group of proteins with identical or similar biological function, expressed in a stage of cell cycle, expressed in a cell type, expressed in a tissue type, expressed in an organ type, expressed in a developmental stage, proteins whose expression and/or activity is altered in a disease or disorder type or stage, or proteins whose expression and/or activity is altered by drug or other treatments.

The present methods and kits can be used in detecting interaction between or among a single test moiety or substance and a plurality of target moieties. Preferably, the present methods are used in high-throughput mode, I.e., in detecting interaction between or among a plurality of test moieties or substances and a plurality of target moieties. The interaction between a plurality of test moieties or substances and a plurality of target moieties can be detected simultaneously or sequentially.

D. Exemplary Embodiments

One objective of certain preferred embodiments of the present invention is to address shortcomings of currently available microarray chips. Another objective of certain preferred embodiments of the present invention is to provide users with a convenient, fast and reliable microarray reaction device.

To achieve the above objectives, the preferred embodiments of the present invention is directed to a microarray reaction device, which comprises: a) a slide with microarrays; b) an enclosure attached to the slide, which separate the slide to form a plurality of isolated microarray areas; and c) a cover comprising a plurality of projections and a supporting structure, wherein a plurality of reaction spaces are formed between the microarray areas of the slide and the projections of the cover, the enclosure is helpful to spatially separate the reaction spaces from each other to avoid cross contamination, and the volumes of the reaction spaces are substantially identical and controllable by the height of the supporting structure and the areas of the projections. There are some through-holes in the cover, each in connection with a reaction space, which make it possible to inject reaction solutions after the cover is pre-positioned on the slide.

The exemplary microarray reaction devices can be used in assaying the interaction between nucleic acids, immunoreactions involving proteins, interactions between a protein and a nucleic acid, a ligand-receptor interaction, and small molecule and protein or nucleic acid interactions.

The slide, the enclosure, or the cover comprises a material selected from the group consisting of silicon, a plastic, a glass, a ceramic, a rubber, a metal, a polymer, a paper and a combination thereof.

The exemplary microarray reaction devices have the following advantages: 1) due to the use of the projections with small surface areas, less sample volume is required leading to cost saving; 2) the use of the supporting structure ensures precise control of the height of the reaction spaces or the thickness of the reaction solutions and consequently, homogeneity of the thickness or volume of the reaction, e.g., hybridization solutions; 3) when multiple samples are assayed, the existence of the multiple reaction spaces, e.g., hybridization, enclosure minimal cross contamination and ensure assay reliability; 4) due to the use of the enclosure, it is unnecessary to search for the microarray positions for attaching probes, thus making the operation more convenient and at the same time increasing assay reliability; 5) the through-holes in the cover make it possible to inject reaction solutions after the cover is pre-positioned on the slide, thus making the operation more convenient and more reliable.

The exemplary microarray reaction device can be used in disease prognosis or diagnosis, life science research, agriculture and environment monitoring, food and hygiene inspection and judicial examination. In particular, the exemplary microarray reaction device can be used with minimal cross contamination. Therefore, the exemplary microarray reaction devices are particularly suited for simultaneous assay of multiple samples and are useful in various prognosis or diagnosis, e.g., simultaneous assay of multiple markers, multiple diseases and/or for multiple patients.

Figure 1B:
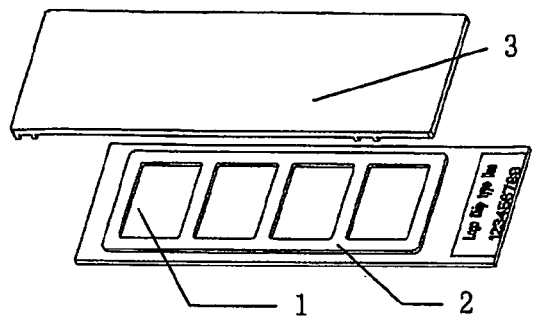
FIG. 1B is an exploded view.
Figure 2A:
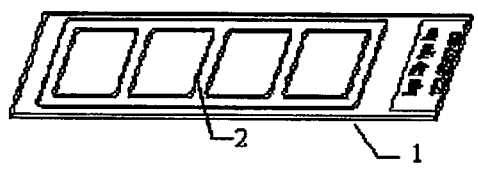
FIG. 2A is a three-dimensional view of the microarray chip.
Figure 2B:
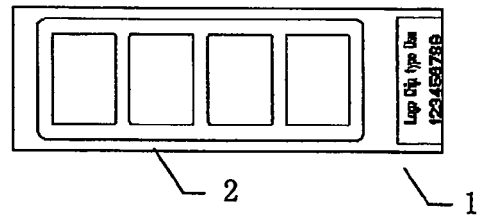
FIG. 2B is a top view.
Figure 3A:
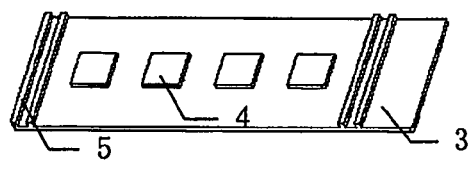
FIG. 3A is a three-dimensional view of the cover.
Figure 3B:
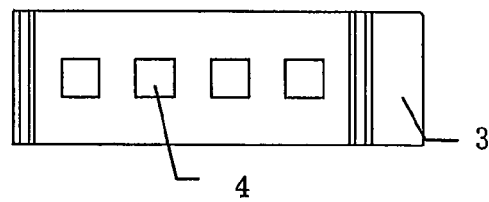
FIG. 3B is a top view.

FIGS. 1-3 illustrate the first embodiment of the present invention. The exemplary microarray reaction device can comprise a slide (1), an enclosure (2), and a cover (3) with a plurality of projections (4) and a supporting structure (5). The slide (1) is divided into many microarray areas by the enclosure (2). The microarray areas, the projections (4) and the supporting structure (5) collectively form the reaction space(s) with controllable thickness and area. The supporting structure (5) can be used to control the relative positions between the microarrays on the slide (1) and the plurality of projections (4) on the cover (3). Same reactions can be carried out in the multiple reaction spaces to assess reliability of assay. Different reactions can be carried out in the multiple reaction spaces to assay multiple samples or markers simultaneously. The enclosure (2) attached to the slide (1) can help to avoid cross contamination and to increase assay accuracy.

FIG. 2 illustrates the slide (1) and the enclosure (2) of one embodiment of the present invention illustrated in FIG. 1. The enclosure (2) is attached to the slide (1) to separate the slide (1) into a plurality of isolated microarray areas. In each area, probes are arrayed. The enclosure (2) is shaped so that the reaction spaces are spatially separated from each other to avoid cross contamination. The thickness of the enclosure ranges from 0.05 mm to 50 mm. The enclosure has a shape selected from the group consisting of a square, a rectangle, a circle, an ellipse, an oval and an irregular shape. The material of the slide (1) may be glass. The material of the enclosure (2) may be a rubber attached to a double-coated tape, and the enclosure is preferably fabricated by stamping. The rubber is silicone, caoutchouc, butyl, urethane, neoprene, etc. The enclosure also may be a single coated tape, and the enclosure is preferably fabricated by stamping. The enclosure (2) can be fixed to the slide (1) by means of process apparatus or manipulator.

FIG. 3 illustrates the cover (3) of the embodiment of the present invention illustrated in FIG. 1. The cover (3) comprises a plurality of projections (4) and a supporting structure (5), wherein a plurality of reaction spaces are formed between the microarray areas of the slide (1) and the projections (4) of the cover (3), and the heights of the reaction spaces are substantially identical and controllable by the height of the supporting structure (5). The height of the projections (4) in the cover ranges from 0.01 mm to 50 mm. The surface of the projections (4) has a shape selected from the group consisting of a square, a rectangle, a circle, an ellipse, an oval and an irregular shape, and has an area ranging from about 1 $mm^2$ to about 600 $mm^2$. The plurality of reaction spaces have a height ranging from about 0.001 mm to about 1 mm, and have a volume ranging from about 0.01 mm$^3$ to about 600 mm$^3$. The material of the cover (3) is preferably a plastic, and the cover (3) is preferably injection molded. The plastic is polycarbonate, methylmethacrylate, polystyrene, bright ABS, polypropylene, etc. The material of the cover (3) is also a glass, and the cover is fabricated by a method selected from the group consisting of gluing, dicing/cutting, slicing, anodic bonding, ultrasonic welding, and a combination thereof.

FIGS. 4-6 illustrate the second embodiment of the present invention. There is a through-hole (6) in connection with each reaction space formed by the microarray area of the slide (1) and the projection (4) on the cover (3). The reaction solution can be injected via the through-hole (6) to the reaction space, after the cover (3) has been pre-positioned on the slide (1). As the reaction solution is injected slowly, it will spread under the projection via capillary action, and the microarray area is covered with a layer of solution which thickness is determined by the reaction space. The through-hole (6) is helpful to avoid the presence of the bubbles and makes the operation more convenient and more reliable. The transverse cross-section of the through-holes has a shape selected from the group consisting of a square, a rectangle, a circle, an ellipse, an oval and an irregular shape. The through-holes in the cover have a diameter ranging from about 0.01 mm to about 100 mm.

Figure 7A:
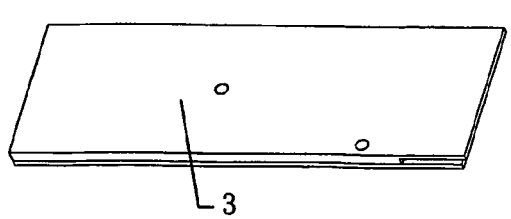
FIG. 7A is an assembly view.
Figure 7B:
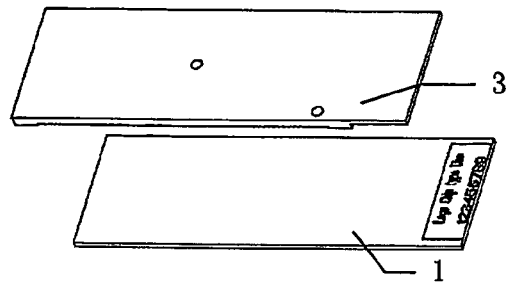
FIG. 7B is an exploded view.
Figure 8A:
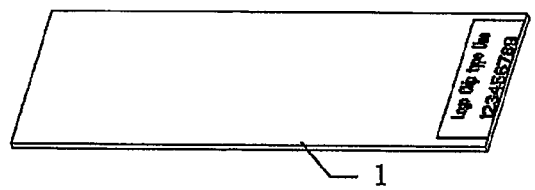
FIG. 8A is a three-dimensional view of the microarray chip.
Figure 8B:
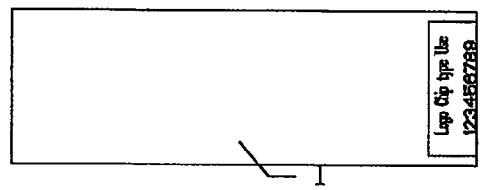
FIG. 8B is a top view.
Figure 9A:
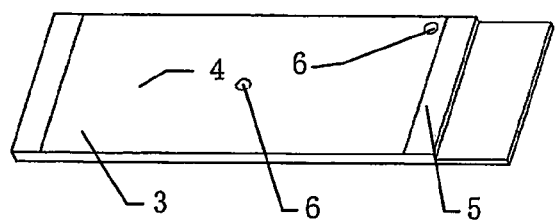
FIG. 9A is a three-dimensional view of the cover.
Figure 9B:
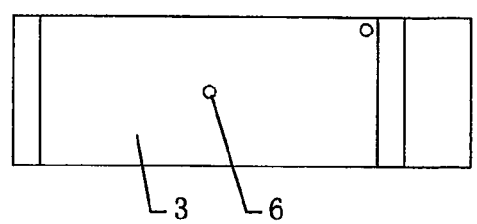
FIG. 9B is a top view.

FIGS. 7-9 illustrate the third embodiment of the present invention, wherein the cover comprises one projection (4), a supporting structure (5), and two through-holes (6). The reaction solution can be injected via the two through-holes (6) to the reaction space, after the cover (3) has been pre-positioned on the microarray chip (1). The microarray chip (1) is a slide The microarray reaction device can be used, when the size of the microarray area is great.

FIGS. 10-12 illustrate the fourth embodiment of the present invention, wherein the cover (3) comprises two projections (4). The diameter of the through-holes (6) is 2 mm.

FIGS. 13-15 illustrate the fifth embodiment of the present invention, wherein the microarray chip (1) comprises one microarray area. The material of the cover (3) is the plastic, and the materials of the microarray chip (1) are a combination of the glass and the plastic.

FIGS. 16-18 illustrate the sixth embodiment of the present invention, wherein the microarray chip (1) comprises one microarray area. The material of the cover (3) is the plastic, and the materials of the microarray chip (1) are a combination of the glass and the plastic.

FIG. 19 is a comparison of the second embodiment of the present invention with a conventional microarray reaction device. FIG. 19A is an image of hybridization results acquired by using the second embodiment of the present invention. FIG. 19B is an image of hybridization results acquired by using the conventional slide and coverslip device. In each image, the four points in the four corners are reference points, the signals of the other points can be normalized by dividing their intensity by an average intensity of the four reference points. In each image, the four points close to the center indicate the same probe, and their average intensity after being normalized can be used as a score of hybridization results. FIG. 19C is a diagram illustrating the difference in the above-described score between FIGS. 19A and 19B, which indicates that the present invention can obtain better signal to noise ratio and make the results more sensitive than conventional slide and coverslip.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The invention claimed is:

1. A microarray reaction device, which device comprises:
   a) a microarray chip comprising a planar surface and an enclosure attached to said microarray chip to form a plurality of microarray areas on said planar surface; and
   b) a cover comprising a plurality of projections and a supporting structure that projects from said cover;
   wherein a plurality of reaction spaces are formed between said microarray areas of said microarray chip and said projections of said cover, wherein the volumes of said reaction spaces are substantially identical and controllable by the height of said supporting structure, the heights of said projections and the areas of said projections, and wherein the thickness of said enclosure is less than the height of said supporting structure.

2. The microarray reaction device of claim 1, wherein the microarray chip is a slide.

3. The microarray reaction device of claim 1, wherein the thickness of the enclosure ranges from about 0.05 mm to about 50 mm.

4. The microarray reaction device of claim 1, wherein the enclosure has a shape selected from the group consisting of a square, a rectangle, a circle, an ellipse, an oval and an irregular shape.

5. The microarray reaction device of claim 1, wherein the cover further comprises a through-hole to deliver fluid into the plurality of reaction spaces.

6. The microarray reaction device of claim 5, wherein the number of the through-holes ranges from about 1 to about 2,500.

7. The microarray reaction device of claim 5, which has identical or different number of the through-holes and the projections.

8. The microarray reaction device of claim 5, wherein the transverse cross-section of the through-holes has a shape selected from the group consisting of a square, a rectangle, a circle, an ellipse, an oval and an irregular shape.

9. The microarray reaction device of claim 5, wherein the through-holes have a diameter ranging from about 0.01 mm to about 100 mm.

10. The microarray reaction device of claim 1, wherein the number of the projections and/or the microarray areas ranges from about 2 to about 2,500.

11. The microarray reaction device of claim 1, which has identical or different number of the projections and the microarray areas.

12. The microarray reaction device of claim 1, wherein the projections and the microarray areas have identical or different shape(s) and/or surface area(s).

13. The microarray reaction device of claim 1, wherein the height of the projections ranges from 0.01 mm to 50 mm.

14. The microarray reaction device of claim 1, wherein the surface of the projections has a shape selected from the group consisting of a square, a rectangle, a circle, an ellipse, an oval and an irregular shape.

15. The microarray reaction device of claim 1, wherein the surface of the projections has an area ranging from about 0.01 mm$^2$ to about 600 mm$^2$.

16. The microarray reaction device of claim 1, wherein the plurality of reaction spaces have a height ranging from about 0.001 mm to about 1 mm.

17. The microarray reaction device of claim 1, wherein the plurality of reaction spaces have a volume ranging from about 0.01 mm³ to about 600 mm³.

18. The microarray reaction device of claim 1, wherein the microarray chip, the enclosure, and/or the cover comprises a material selected from the group consisting of a silicon, a plastic, a glass, a ceramic, a rubber, a metal, a polymer, a paper and a combination thereof.

19. The microarray reaction device of claim 1, wherein the cover comprises a plastic.

20. The microarray reaction device of claim 19, wherein the cover is injection molded.

21. The microarray reaction device of claim 19, wherein the plastic is selected from the group consisting of polycarbonate, methylmethacrylate, polystyrene, acrylonitrile-butadiene-styrene (ABS), polyethylene and polypropylene.

22. The microarray reaction device of claim 1, wherein the cover comprises a glass.

23. The microarray reaction device of claim 22, wherein the cover is fabricated by a method selected from the group consisting of gluing, dicing/cutting, slicing, anodic bonding, ultrasonic welding, and a combination thereof.

24. The microarray reaction device of claim 1, wherein the enclosure comprises a rubber attached to a double-coated tape.

25. The microarray reaction device of claim 24, wherein the enclosure is fabricated by stamping.

26. The microarray reaction device of claim 24, wherein the rubber is selected from the group consisting of silicone, caoutchouc, butyl, urethane and neoprene.

27. The microarray reaction device of claim 1, wherein the enclosure comprises a single coated tape.

28. The microarray reaction device of claim 27, wherein the enclosure is fabricated by stamping.

29. The microarray reaction device of claim 1, wherein a reactant capable of binding to an analyte is immobilized in a microarray area.

30. A microarray reaction device, which device comprises:
a) a microarray chip comprising a planar surface and an enclosure attached to said microarray chip to form a microarray area on said planar surface;
b) a cover comprising a projection and a supporting structure that projects from said cover; and
wherein a reaction space is formed between said microarray area of said microarray chip and said projection of said cover, wherein the volumes of said reaction space is controllable by the height of said supporting structure, the height of said projection and the area of said projection, and wherein the thickness of said enclosure is less than the height of said supporting structure.

* * * * *